United States Patent [19]

Meyer

[11] 4,022,190
[45] May 10, 1977

[54] APPARATUS FOR SENSING PRESSURE

[75] Inventor: Glenn A. Meyer, Brookfield, Wis.

[73] Assignee: Hittman Corporation, Columbia, Md.

[22] Filed: July 16, 1974

[21] Appl. No.: 489,000

[52] U.S. Cl. .................................. 128/2 A; 73/393; 73/406; 128/2.05 D; 128/2.05 E; 250/336
[51] Int. Cl.² .................................. A61B 5/00
[58] Field of Search ......... 128/2 A, 2.05 D, 2.05 E, 128/350 R, 350 V, 1 R; 73/406, 393, 409, 410, 407; 250/336 R

[56] References Cited
UNITED STATES PATENTS

| 3,034,356 | 5/1962 | Bieganski et al. ............ 128/2.05 E |
| 3,503,402 | 3/1970 | Schulte .......................... 128/350 V |
| 3,625,199 | 12/1971 | Summers .................. 128/2.05 E X |
| 3,625,199 | 12/1971 | Summers ...................... 128/2.05 E |
| 3,686,958 | 8/1972 | Porter et al. ....................... 73/406 |
| 3,693,407 | 9/1972 | McWhorter et al. ...... 128/2.05 D X |
| 3,693,612 | 9/1972 | Donahoe et al. .............. 128/2.05 D |
| 3,789,667 | 2/1974 | Porter et al. ......................... 73/406 |

Primary Examiner—Kyle L. Howell
Attorney, Agent, or Firm—Fleit & Jacobson

[57] ABSTRACT

A pressure sensor apparatus primarily for sensing pressure in a body cavity such as the cranium, bladder or vena cava of an animal or human comprising a housing having a diaphragm dividing the interior of the housing into two chambers. A member containing filter material is connected to the housing and communicates with one of the chambers formed in the housing. The other chamber contains radioactive fluid and is connected to a variable volume chamber that receives a volume of radioactive fluid which is proportional to the pressure sensed by the flexible member. A radiation detector senses the volume of radioactive fluid in the variable volume chamber.

16 Claims, 3 Drawing Figures

U.S. Patent    May 10, 1977    4,022,190

APPARATUS FOR SENSING PRESSURE

CROSS-REFERENCE TO RELATED APPLICATION

This application is related to commonly assigned application Ser. No. 478,763, filed June 12, 1974, for PRESSURE SENSOR APPARATUS, by Thomas S. Bustard et al., now abandoned.

BACKGROUND OF THE INVENTION

The need for a non-invasive technique for measuring the pressure in body cavities of animals or humans is recognized as highly desirable for continuous or intermittent monitoring of body conditions. Such cavities as the cranium, vena cava, bladder, and others provide valuable and sometimes critical information for maintaining the well being or survival of an animal or human. For example, it is known that intracranial pressure provides a valuable indication of well being for a variety of clinical conditions.

A long-term, non-invasive monitor of intracranial pressure is particularly desirable for the congenital hydrocephalic. This condition is one in which the normal production of cerebrospinal fluid is not balanced by reabsorption of the fluid. The retained fluid increases the intracranial pressure and causes head swelling which is a characteristic of hydrocephalus. The increase in intracranial pressure can eventually lead to disability or death.

The normal treatment for hydrocephalus comprises surgically implanting a fluid shunt to transfer cerebrospinal fluid from the intracranial cavity to other parts of the body such as the peritoneal cavity or the jugular vein. The surgically implanted shunt is basically a drainage tube which contains a check valve and requires a modest pressure differential for the cerebrospinal fluid to flow. These shunts often become partially or even fully blocked and intracranial pressure starts to rise resulting in intracranial hypertension.

The symptoms characteristic of a blocked shunt are also characteristic of various other maladies. Early symptoms of a clogged shunt are nausea, headache, and dizziness, any of which can result from any other causes other than intracranial hypertension. In young children especially a physician cannot easily determine shunt blockage without performing a surgical procedure. The presence of an indwelling pressure sensor would permit the physician to directly monitor the intracranial pressure and remove a substantial amount of risk from his diagnosis.

An additional problem associated with a blocked vent is the rate at which the pressure can rise. Drastic increases can occur within less than an hour. Since a high pressure that is maintained for a period of time will cause irreversible brain damage, it is imperative that pressure increases be discovered in the shortest possible time. Full utilization of a pressure sensor requires a simplified determination of the pressure so that even a parent can perform the determination.

Against this background, there is a recognized and long felt need for a device which overcomes the aforementioned disadvantages and provides a sensor having a self-contained, long-term energy source with compensation for ambient pressure variations and low sensitivity to temperature changes.

The pressure sensor of the present invention is designed to eliminate many of the previously mentioned problems. Once the pressure sensor is installed by a competent surgeon, the pressure can be read non-invasively by a physician with a minimal amount of special equipment. If an attending physician is not readily available, equipment can be installed in the child's home and the parents instructed in its use.

SUMMARY OF THE INVENTION

The pressure sensor of the present invention is fully implantable and contains a radioactive fluid so that the pressure can be readout non-invasively. In its preferred form, the sensor system comprises two fluid-filled chambers separated by a flexible diaphragm. Non-radioactive fluid from the body cavity being sensed is contained in the first chamber which is in communication with the body cavity and exposed to the pressure to be sensed. The two chambers are located external to the cavity being sensed and preferably situated just under the skin. The pressure acting upon the flexible member causes the flexible diaphragm separating the two chambers to deflect and the radioactive fluid contained in the second chamber to deflect and the radioactive fluid contained in the second chamber or fluid reservoir to be transferred to a sensor reservoir. The movement of fluid into the sensor reservoir is sensed from outside the skin by a conventional nuclear counter or crystal detector instrument.

The application of the present invention to hydrocephalus greatly facilitates treatment of the defect. The pressure sensor of the present invention when used as an intracranial pressure sensor device has a long life, is fully implantable and does not require any energy source other than the radioactive fluid contained in the device. Two of the major advantages of the present invention are the elimination of implanted energy sources, such as batteries, to operate the device, and the elimination of leads or other penetrations through the skin to provide power or transmit a signal. With a long-lived radioisotope such as promethium 145, the inventive pressure sensing device can be fully implanted and left in place for the life of the patient. Furthermore, the invention contemplates a design and a selection of materials that will assure a negligible radiation dosage to the patient. Although in this application, the invention is primarily intended for a long-term implantation in hydrocephalic children, one may easily appreciate its value in short-term monitoring of head trauma patients.

The inventive pressure monitoring system can be fully implanted with no tubing or wires penetrating the skin, functions accurately to within several millimeters of water pressure and is unaffected by variations in ambient pressure. Also, it is generally insensitive to ambient temperature. Furthermore, the materials used to construct the devices according to the present invention are biologically inert and do not pose any health hazard to the animal or human subject or make the subject more susceptible to mechanical trauma. The sensor unit is of relatively small size and so does not produce unsightly bulging when implanted subdermally.

Other features and advantages of the invention will be apparent from the following description of the preferred embodiments of the invention as shown in the accompanying drawings.

BRIEF DESCRIPTIONS OF THE DRAWINGS

DESCRIPTION OF THE PREFERRED EMBODIMENTS

Figure 1:
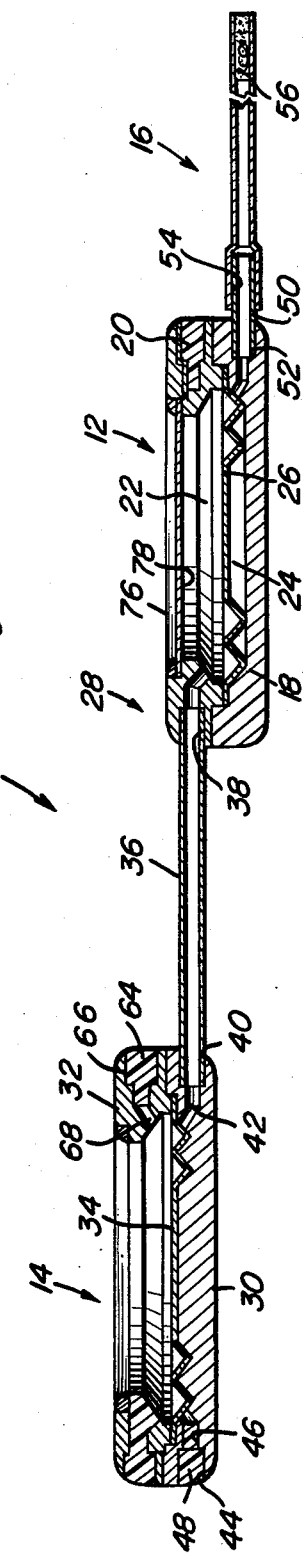
FIG. 1 is a vertical, cross-sectional view of one embodiment of the pressure sensor apparatus of the present invention.
Figure 2:
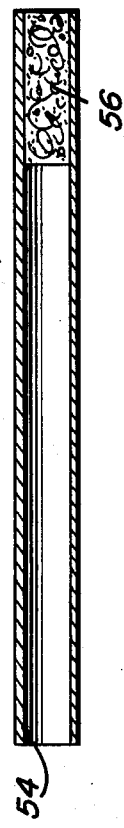
FIG. 2 is an enlarged cross-sectional view, of the shunt tube shown in FIG. 1.

Pressure sensor 10 broadly comprises shielded housing 12, unshielded housing 14 and shunt tube 16. Base 18 and top 20 of shielded housing 12 define an interior opening which is divided into upper and lower chambers 22 and 24, respectively, by diaphragm 26. Chamber 22 acts as a reservoir for radioactive fluid and is shielded by shield plate 28.

Unshielded housing 14 comprises base 30 and top 32. Base 30 has a convoluted upper surface which mates with a correspondingly convoluted diaphragm 34. Chamber 22 is fluidly connected to housing 14 by means of tube 36 which fits into ports 38 and 40 of housings 12 and 14, respectively. As radioactive fluid enters housing 14, it passes through conduit 42 and between disphragm 34 and the upper surface of base 30. More specifically, diaphragm 34 and the upper surface of base 30 are together adapted to form a chamber for receiving radioactive fluid. Port 44 is provided in housing 14 for filling sensor 10 with radioactive fluid through conduit 46. Port 44 is sealed with plug 48 during use. Chamber 24 is fluidly connected to shunt tube 16 by means of tube 50 which fits into port 52 of housing 12 and into opening 54 in the end of shunt tube 16.

The end of shunt tube 16 is filled with filter material 56 and is placed in the body cavity such as the cranium, bladder, or vena cava of an animal or human for sensing the pressure of the body cavity. Shunt tube 16 is typically formed from silicone rubber such as the elastomer sold under the trademark Silastic but any other material can be used which is substantially impermeable to the body fluid and compatible with body tissue. Shunt tube 16 has an outside diameter of about 2.5 millimeters and an inside diameter of about 1.5 millimeters. Filter material 56 is any porous material which is compatible with body tissue and will permit the transmission of body fluid but will prevent particulate matter present in the body cavity such as fibroblasts from entering chamber 24. A suitable commercially available filter material is sold under the trademark Millipore. In general, filter material 56 should be capable of filtering particulate matter above about 5 micron.

Sensor 10 is preferably constructed so that it is only responsive to pressure changes in the body cavity being sensed and is not responsive to ambient pressure changes which are exerted equally on both shunt tube 16 and diaphragm 34. In the embodiment shown in FIG. 1, diaphragm 34 is directly exposed to the ambient pressure. In the alternative embodiment shown in FIG. 3, plate 60 is attached to top 32 of unshielded housing 14 to provide enclosed chamber 62 above diaphragm 34. Plug 64 closing port 66 and conduit 68 in housing 14 is removed and tambour 70 fluidly attached to chamber 62 by means of tube 72. Tube 72 fits into port 66 and opening 74 in the end of tambour 70. Tambour 70 is filled with a non-radioactive fluid such as water. Accordingly, changes in ambient pressure will be exerted equally on both shunt tube 16 and tambour 70 making sensor 10 responsive only to changes in body cavity pressure.

Figure 3:
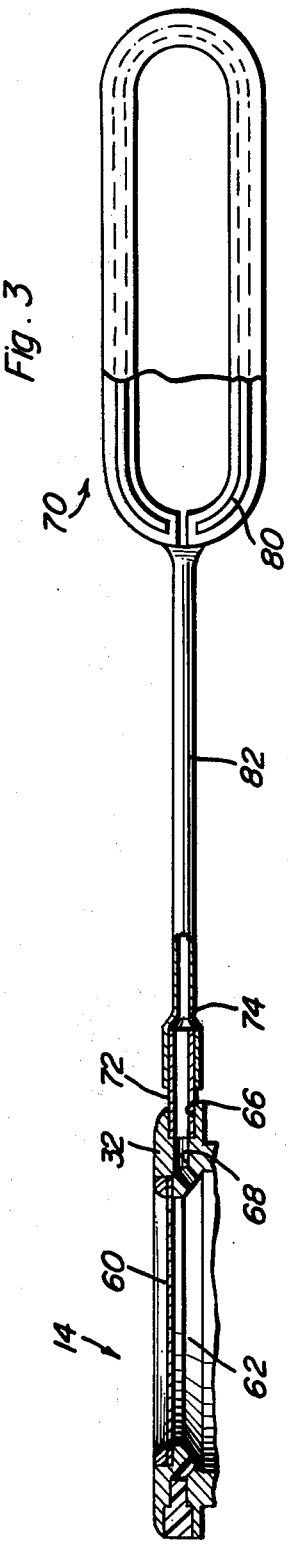
FIG. 3 is a vertical, cross-sectional view of an alternative embodiment of a portion of the housing for the sensor reservoir shown in FIG. 1.

Tambour 70 must be constructed of a flexible material so that it will be responsive to pressure changes and a material which is impermeable to the non-radioactive fluid and in particular to water. A desirable material from the standpoint of flexibility is silicone rubber. Butyl rubber which has a low diffusion coefficient for water is also a suitable material from which the tambour can be fabricated. Tambour 70 is essentially a flexible container or sack which can be formed in any suitable shape such as cylindrical, disc-shaped, spheroidal or planar. As shown in FIG. 3, wire 80 can be placed in tambour 70 to give it suitable shape. Furthermore, a coiled spring (not shown) can be placed in neck portion 82 of tambour 16.

Bases 18 and 30 and tops 20 and 32 of housings 12 and 14, respectively, are preferably constructed of titanium and suitably secured together by bolts, screws or the like. The convoluted diaphragms shown in the embodiment of FIG. 1 are preferably constructed of an elastomer such as silicone or butyl rubber. In the case of butyl rubber, it may be desirable to use a leaf spring in conjunction therewith to prevent cold flow. Tubings 36 and 50 are also preferably constructed of titanium. Plugs 48 and 64 are also preferably constructed of a elastomer such as silicone rubber. Shield plate 24 preferably comprises a tantalum plate 76 approximately 20 mils thick; however, tungsten, iridium, rhenium, platinum, rhodium, gold, niobium, or other suitable heavy metals at least about 7 to 10 mils thick can be used. The lower surface of shield plate 28 is preferably covered with a very thin titanium layer 78. Wire 80 in tambour 70 is preferably constructed of tantalum. All tubing, housing and diaphragm joints are suitably formed by brazing or the use of suitable gaskets, etc. Finally, the entire sensor can be coated with a thin coating of silicone rubber or placed in a silicone rubber boot if desired to provide better tissue compatibility.

Change in pressure of the body cavity being monitored cause body fluid to flow through shunt tube 16 and into chamber 24 in shielded housing 12. Filter material 56 filters particulate matter from the body fluid. Unshielded housing 12 provides a mechanical interface between the non-radioactive, pressure sensing fluid (body fluid) and the radioisotope bearing fluid. Diaphragm 26 separates the two fluids and provides part of the force necessary to balance the body cavity pressure. As diaphragm 26 deflects under increasing body cavity pressure, it forces radioactive fluid out of the radioactive fluid reservoir formed by chamber 22, through connecting tube 36 and between diaphragm 34 and the upper surface of base 30 of nonshielded housing 14. This forces convoluted diaphragm 34 to deflect, also adding to the force exerted to balance the body cavity fluid pressure. Convoluted diaphragm 34 serves to permit fluid transfer while also keeping out essentially all fluid when the body cavity is at its normal pressure. As the pressure of the body cavity increases more fluid enters housing 14. Since the amount of fluid in the sensor reservoir formed between diaphragm 34 and the upper surface of base 30 is a function of the body cavity pressure, and the count rate is directly dependent on the fluid quantity, the body cavity pressure can immediately be determined via the count rate.

Because of the unique construction of pressure sensor 10, no external leads are required and the sensor occupies very little space under the scalp so that it produces only a slight elevation thereof. Shunt tube 16 can be placed through a burr hole within a cerebral ventrical and housings 12 and 14 are positioned outside the skull, but implanted under the scalp. A change in the volume of radioactive fluid in housing 14 is detected by measuring the change in radioactivity immediately adjacent to the skin. Thus, the skin does not have to be penetrated to obtain reliable pressure information. The quantity of the radioisotope utilized in the device is extremely small, typically less than one microcurie and results in surface dose rates to the scalp and skull which are on the order of 100 times less than the rates necessary to cause detectable changes in the most radiosensitive body tissue and thus will not adversely affect the adjacent skin or bone marrow.

The radioisotope used in the present invention should have a half life which is sufficiently long to give acceptable end-of-life pressure data. The radioisotope should also be safe as a source of radiation when used immediately beneath the scalp or within a body cavity so that no damage will occur if it is inadvertently released into the body. Another requirement is that the radioisotope must be detected efficiently which means that it must have a high skin transmissibility as well as a high detector efficiency. In addition, the radioisotope must be chemically compatible with and must remain in solution within the radioactive fluid chambers.

The preferred radioisotope used in the present invention is promethium 145. Promethium has an 18 year half life and a soft gamma emission which can be easily transmitted through the skin and efficiently detected while being safely used in quantities necessary for statistical counting accuracy. Among other radioisotopes which can be used in the invention is holmium 163 which has a 40 to 60 year half life.

A nuclear counter or crystal detector is placed directly over housing 14. Interference from the radioactive fluid in chamber 22 is eliminated by the use of tantalum shielding 28. The count rate determined by the detector is converted to pressure by use of a simple graph or table or by any automatic means.

While the pressure sensor of the present invention has been illustrated primarily as an intracranial pressure sensor, it should be understood that the sensor is also useful in other body cavities in the treatment or care of animals and humans. Thus, valuable information may be derived from monitoring pressure in the vena cava, bladder, or some other body cavity, the foregoing details with respect to intracranial pressure being but a specific illustration of the application of the present invention to a particular problem and, in that sense, illustrative rather than limiting. Furthermore, while the preferred embodiments of the invention have been disclosed, it should be understood that the invention is not limited to such embodiments. For example, in certain applications shunt tube 16 can be eliminated and filter material 56 placed in the inlet to chamber 24. Accordingly, the present invention should only be limited as defined in the appended claims.

What is claimed is:

1. A fluid pressure sensor apparatus comprising a housing, a first resilient means dividing said housing into first and second chambers, fluid communication means for placing said first chamber in fluid communication with the fluid whose pressure is to be sensed so that the pressure of said fluid will cause said first resilient means to move, filter means associated with said fluid communication means for preventing particulate matter in said fluid from entering said first chamber, second resilient means in fluid communication with said second chamber, and a radioactive fluid contained within said second chamber and being in fluid communication with said second resilient means, said radioactive fluid being transferred from said second chamber as a function of the fluid pressure acting upon said first resilient means.

2. The apparatus of claim 1 in which said second resilient means acts to at least partially define a third chamber.

3. The apparatus of claim 2 in which said housing acts to define at least a portion of said third chamber.

4. The apparatus of claim 2 and further comprising a second housing which acts to define at least a portion of said third chamber.

5. The apparatus of claim 4 in which said second housing has at least one convoluted surface and said second resilient means comprises a convoluted diaphragm associated with said second housing and having its convolutions adapted to snugly fit in the convolutions of said convoluted surface, said convoluted diaphragm being adapted to move away from the convolutions of said convoluted surface to form said third chamber.

6. The apparatus of claim 1 in which said first resilient means is a convoluted diaphragm.

7. The apparatus of claim 1 in which said fluid communication means comprises a tube.

8. The apparatus of claim 1 in which said filter means comprises a porous material which is compatible with body tissue and will permit the transmission of body fluid but will prevent the passage of particulate matter present in said body fluid.

9. The apparatus of claim 1 in which said radioactive fluid is promethium 145.

10. The apparatus of claim 1 in which said second chamber has radiation shielding associated therewith.

11. The apparatus of claim 1 in which said second resilient means has means associated therewith so that said apparatus is insensitive to changes in ambient pressure.

12. In a pressure sensor apparatus for sensing fluid pressure in a body cavity, the improvement comprising fluid communication means for placing said pressure sensor apparatus in communication with the fluid whose pressure is to be sensed and filter means associated with said fluid communication means for filtering particulate matter in said fluid.

13. The apparatus of claim 12 in which said pressure communication means comprises a tube.

14. The apparatus of claim 13 in which said filter means comprises filter material capable of filtering particulate matter above about 5 micron.

15. A pressure sensor apparatus comprising a housing, resilient means dividing said housing into first and second chambers, fluid communication means for placing said first chamber in communication with the fluid whose pressure is to be sensed so that the pressure of said fluid will cause said resilient means to move, filter means associated with said fluid communication means for preventing particulate matter in said fluid from entering said first chamber, and a radioactive material contained within at least said second chamber, said radioactive material being associated with said resilient means so that it is moved as a function of the fluid pressure acting upon said resilient means.

16. In a pressure sensor apparatus for sensing fluid pressure in a body cavity, the improvement comprising an elastomeric tube for placing said pressure sensor apparatus in communication with the fluid whose pressure is to be sensed and filter material which is compatible with body tissue and will permit the transmission of body fluid filling the end of the tube for filtering particulate matter in said fluid, said filter material being capable of filtering particulate matter above about 5 micron.

* * * * *